United States Patent [19]
Tsuboi

[11] Patent Number: 5,216,921
[45] Date of Patent: Jun. 8, 1993

[54] METHOD AND APPARATUS FOR DETECTING DEFECTS AND DIFFERENT-HARDNESS PORTIONS OF AN OBJECT WITH PROTRUSIONS

[75] Inventor: Kiyoshi Tsuboi, Tokyo, Japan

[73] Assignee: Honda Giken Kogyo Kabushiki Kaisha, Tokyo, Japan

[21] Appl. No.: 679,960

[22] Filed: Apr. 3, 1991

[30] Foreign Application Priority Data

Apr. 6, 1990 [JP] Japan .................. 2-91754

[51] Int. Cl.⁵ .......................... G01N 29/12
[52] U.S. Cl. ...................... 73/579; 73/646; 364/508
[58] Field of Search ........... 73/579, 582, 583, 592, 73/602, 645, 646, 658, 659; 364/508

[56] References Cited

U.S. PATENT DOCUMENTS

| | | | |
|---|---|---|---|
| 2,486,984 | 11/1949 | Rowe | 73/582 |
| 3,916,699 | 11/1975 | Moran et al. | 73/623 |
| 4,805,457 | 2/1989 | Oates et al. | 73/659 |
| 5,062,296 | 11/1991 | Migliori | 73/579 |

FOREIGN PATENT DOCUMENTS 0274865 7/1988 European Pat. Off. .
2139756 11/1984 United Kingdom .

OTHER PUBLICATIONS

"Development of an Improved Sonic Resonance Inspection System for Nodularity in Crankshafts" by B. V. Kovacs, Y. Stone and E. P. Papadakis, Materials Evaluation/42/Jun. 1984, pp. 906-915.

Primary Examiner—Hezron E. Williams
Assistant Examiner—Rose M. Finley

[57] ABSTRACT

A test object having a plurality of protrusions is inspected for a defect and/or different-hardness by applying vibration to the test object. Spectral data of the vibration of the test object is analyzed based on signals indicative of the vibration of the protrusions. Spectral energy peaks are then detected in different spectral frequency regions corresponding respectively to the protrusions based on the signals. It is then determined whether there are two separate spectral energy peaks in the spectral region corresponding to each of the protrusions, thereby to determining whether there is a defect and/or different-hardness portion in each of the protrusions.

14 Claims, 9 Drawing Sheets

FIG.1

POSITION INDICATED BY "1" IN FIG. 7

METHOD AND APPARATUS FOR DETECTING DEFECTS AND DIFFERENT-HARDNESS PORTIONS OF AN OBJECT WITH PROTRUSIONS

BACKGROUND OF THE INVENTION

1. Field of the Invention

The present invention relates to a method of and an apparatus for detecting a defect and a portion having a different-hardness in a test object which has a plurality of protrusions, and more particularly to a method of and an apparatus for detecting which of a plurality of protrusions of a test object has a defect and/or different-hardness therein.

2. Prior Art

Many automotive components are formed by castings. If these components have defects such as cracks, cavities, recesses, or the like, the components tend to be destroyed in use. Any defective components should preferably be detected and rejected from the production line before the components are assembled into automobiles. Detection of the positions of defects in components is helpful in determining the cause of the defects.

If a defect-free cast-iron component has a localized spherical mass of graphite in the cast-iron structure, and the graphite mass is harder than the rest of the component, then a crack or a cavity tends to develop from the harder graphite mass while the component is in use. Components with such localized portions of different hardness should also be rejected from the production line.

Various nondestructive testing methods are known for detecting those defects in engine components. For example, engine component deficiencies have been detected by an ultrasonic echo method, an acoustic emission method which detects a sonic energy wave caused when a crack is produce in a component, a CCD camera image observation method, a radiographic method, and a visual-optical method using a color check, among others.

There have been available many non-destructive processes for determining whether there is a different-hardness mass in a test object.

The ultrasonic echo method uses a transducer or sensor for transmitting and receiving ultrasonic energy into and from a test object. In use, the sensor is held in contact with the test object. Since, however, the ultrasonic energy is propagated linearly through the test object, only the area of the test object which is contacted by the sensor can be tested at a time. The waveform of the ultrasonic energy received from the test object tends to vary due to reflections caused by inadequate coupling between the sensor and the test object or due to slight changes in the angle of the sensor with respect to the test object. Consequently, it is not easy to achieve proper determination of defects in test objects.

The acoustic emission method also employs a sensor held in contact with a test object. Inasmuch as a crack is detected on the basis of an acoustic emission signal produced when the crack is caused, a crack can be detected only while the crack is being developed. Difficulty arises in this testing method unless the a crack to be detected is increasing in a test object.

The CCD camera image observation method is liable to detect discolored spots and patterns other than real defects and is not effective to detect cavities known as blowholes in castings. It is impossible to detect the position of a defect in a test object, using a CCD camera.

The radiographic method allows the operator to make a visual inspection of the internal structure of a test object. However, it is cumbersome to regulate the dose of X-rays to be applied to a test object. A crack in a test object may not be observed if the dose of applied X-rays is not properly regulated.

Since this method has been unable to detect any different-hardness portion in a test object, products with different-hardness regions cannot be rejected from the production line.

If test objects have a plurality of protrusions, each protrusion has to be inspected. It would be timeconsuming and cumbersome to test all test objects with protrusions that needed to be tested. Any conventionally available test method for inspecting test objects with protrusions are suitable for inspection on production lines.

SUMMARY OF THE INVENTION

It is an object of the present invention to provide a method of and an apparatus for easily and simply non-contactually detecting a defect and a portion having a different-hardness and the positions in a test object which has a plurality of protrusions.

According to the present invention, there is provided a method of detecting a defect and/or different-hardness in a test object having a plurality of protrusions, comprising the steps of applying vibration to a test object having a plurality of protrusions, analyzing spectral data of the vibration of the test object based on signals indicative of the vibration of the protrusions, detecting spectral energy peaks of different spectral frequency regions corresponding respectively to the protrusions based on the signals, and determining whether there are two separate spectral energy peaks in the spectral region corresponding to each of the protrusions thereby to determine whether there is a defect and/or different-hardness in each of the protrusions.

According to the present invention, there is also provided an apparatus for detecting a defect and/or different-hardness in a test object having a plurality of protrusions, comprising vibrating means for vibrating a test object having a plurality of protrusions, detecting means for detecting vibration of the test object and converting the detected vibration into an electric signal, means responsive to the electric signal from the detecting means, for analyzing a spectrum of the vibration of the test object to detect spectral energy peaks in respective spectral frequency regions corresponding respectively to the protrusions, and determining means for determining whether there are two separate spectral energy peaks in each of the spectral frequency regions.

The above and other objects, features and advantages of the present invention will become more apparent from the following description when taken in conjunction with the accompanying drawings in which a preferred embodiment of the present invention is shown by way of illustrative example.

DETAILED DESCRIPTION OF THE PREFERRED EMBODIMENT

A method of detecting a defect and different-hardness in a test object according to the present invention is basically characterized by vibrating the test object and detecting whether there are a defect and a different-hardness in the test object or not based on the vibration of the test object. First, the fundamental principles of the defect detecting method will be described below.

The vibration of a vibrated test object having a plurality of protrusions can be detected without contact with the test object. It has been found that a spectrum of the detected vibration includes spectral energy peaks at frequencies depending on the volume of the protrusions in a 1:1 correspondence to the protrusions, and that if there is a defect and/or a different-hardness portion (which may be of foreign matter) in each of the protrusions the spectrum has two spectral energy peaks in each spectral region corresponding to the protrusions.

The above findings are explained below.

When vibrated, each protrusion produces a natural vibration depending on the volume thereof, and the spectrum includes a spectral energy peak in a spectral region which has in a 1:1 correspondence to the protrusion. If there is no defect or different-hardness in the protrusion, there is only one energy peak in the corresponding spectral region.

If there is a defect in the protrusion, since the vibration is not transmitted through the defect, it is propagated through a path that bypasses the defect. Therefore, the vibratory energy is divided into the energy of a natural vibration and the energy of vibration propagated through the bypassing path. Since the bypassing path is longer than the path of the natural vibration, the spectral energy peak of the vibration through the by-passing path is located at a frequency lower than the frequency of the natural vibration. Therefore, the spectral region corresponding to the protrusion has two separate energy peaks.

In a substance, vibration is propagated at a velocity depending on the hardness of the substance. The higher the hardness, the faster the vibration is propagated in the substance. If a protrusion has a harder local portion therein, then the harder portion increases the velocity of propagated vibration. Therefore, the vibratory energy is divided into the energy of a natural vibration and the energy of vibration passing through the harder portion. Consequently, the spectral region corresponding to the protrusion has two separate energy peaks. If a harder portion is present in the protrusion, then the spectral region contains an energy peak of a fundamental natural vibration and an energy peak at a higher frequency. If a softer portion is present in the protrusion, then the spectral region contains an energy peak of fundamental natural vibration and an energy peak at a lower frequency.

As a result, whether each protrusion of a test object has a defect and/or a different-hardness portion can be detected by checking if the spectral region corresponding to the protrusion contains two energy peaks or not.

A method of detecting a defect and a different-hardness portion in a component (hereinafter referred to as a "test object") based on the above principles will be described below.

Figure 1:
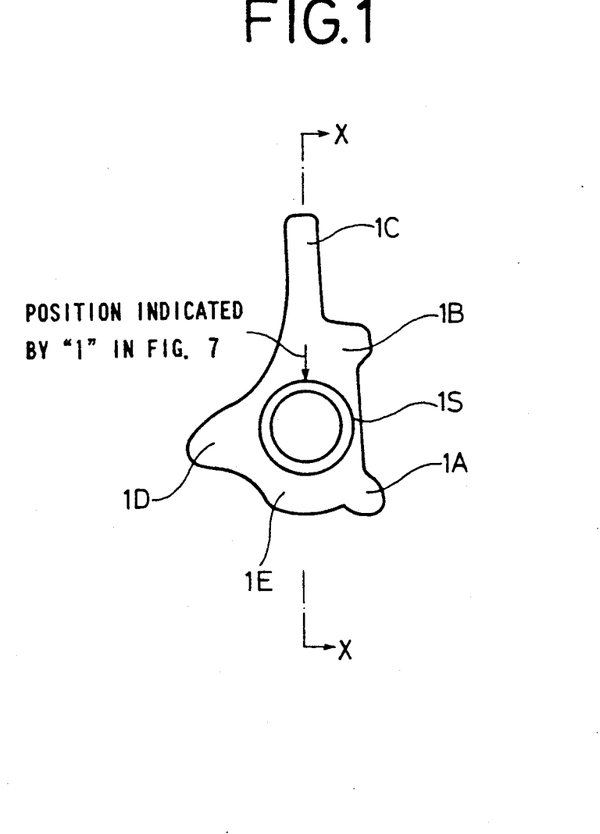
FIG. 1 is a plan view of a test object with a plurality of protrusions to be inspected.
Figure 2:
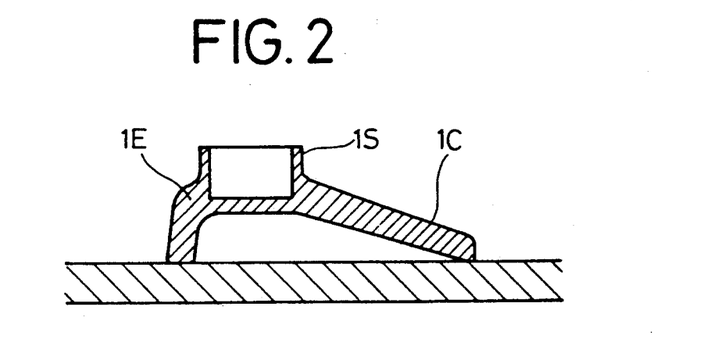
FIG. 2 is a cross-sectional view taken along line II—II of FIG. 1.

As shown in FIG. 1, a test object has a central cylindrical protrusion 1S and first through fifth protrusions 1A, 1B, 1C, 1D, 1E projecting radially outwardly from the cylindrical protrusion 1S. As shown in FIG. 2, the test object is placed on a table T made of hard rubber, for example.

The test object on the table T is vibrated by application of an impact thereto. Vibration of the test object is detected by a displacement meter or a vibration sensor with sharp directivity, and the spectrum of the natural vibration of the test object is analyzed. The spectrum includes a plurality of spectral energy peaks in respective spectral frequency regions which correspond respectively to the protrusions 1S, 1A, 1B, 1C, 1D, 1E with respect to each vibration of first order, second order, and so on.

Figure 3A:
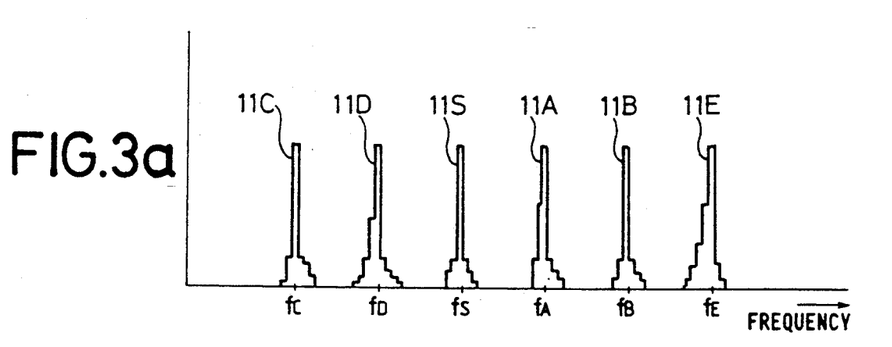
FIGS. 3A and 3B are diagrams of spectral waveforms illustrating the principles of a method according to the present invention.

FIG. 3A shows a spectrum of first-order vibration in case there is no defect and different-hardness portion in a test object.

As shown in FIG. 3A, when vibrated, the protrusions 1S, 1A, 1B, 1C, 1D, 1E produce inherent natural vibrations of first order, second order, and so on. The natural vibrations of these protrusions have frequencies fS, fA, fB, fC, fD, fE determined according to the shapes and volumes of the protrusions. The frequencies fS, fA through fE of the natural vibrations depend on the volume of the protrusion, and are inversely proportional to the lengths of the protrusions provided the protrusions have substantially the same thicknesses and widths. The lengths of the protrusions are measured from the center of the vibrations, i.e., the center of the cylindrical protrusion 1S, to the radially outer tip end of the protrusion. In FIG. 3A, a spectral energy peak 11C at the lowest frequency corresponds to the protrusion 1C, a spectral energy peak 11D to the protrusion 1D, a spectral energy peak 11S to the protrusion 1S, a spectral energy peak 11A to the protrusion 1A, a spectral energy peak 11B to the protrusion 1B, and a spectral energy peak 1E to the protrusion 11E.

The above spectra data are produced if the test object is free of any defects and different-hardness portions. If there is a defect and/or a different-hardness portion in the test object, the spectrum of the vibration of the test object contains two spectral energy peaks at close frequencies in the spectral region corresponding to that protrusion. The reason for such two spectral energy peaks is as follows:

If a crack is present as a defect in a protrusion of a test object, then the vibratory wave cannot pass through the crack, but bypasses the crack. The vibratory energy in the protrusion is thus divided into the energy of a natural vibration and the energy of a vibration propagated through a path bypassing the crack. Since the bypassing path is longer than the path of the natural vibration, the spectral energy peak of the vibration through the bypassing path is located at a frequency lower than the frequency of the natural vibration. Therefore, the spectral region corresponding to the protrusion has two separate energy peaks.

Figure 3B:
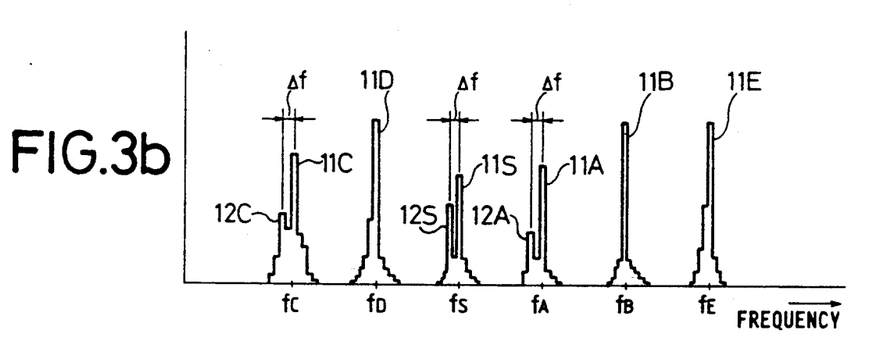

FIG. 3B shows a first-order spectrum produced when there ar defects or different-hardness portions in the protrusions 1A, 1C, 1S, the spectrum including spectral energy peaks 12A, 12C, 12S induced by the defects or different-hardness portions. The sizes of the defects or different-hardness portions are proportional to the difference $\Delta f$ between the frequencies of the two energy peaks in each of the spectral regions. The sizes of the defects or different-hardness portions correspond to the volumes thereof.

Figure 4A:
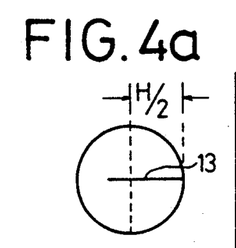
FIGS. 4A and 4B are diagrams showing cracks in test objects.
Figure 4B:
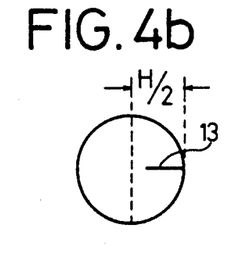
Figure 5A:
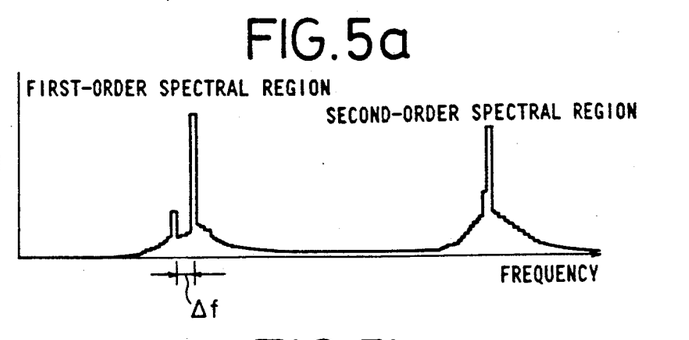
FIGS. 5A and 5B are diagrams showing spectral energy peaks in first- and second-order spectral regions produced by the cracks shown in FIGS. 4A and 4B.
Figure 5B:
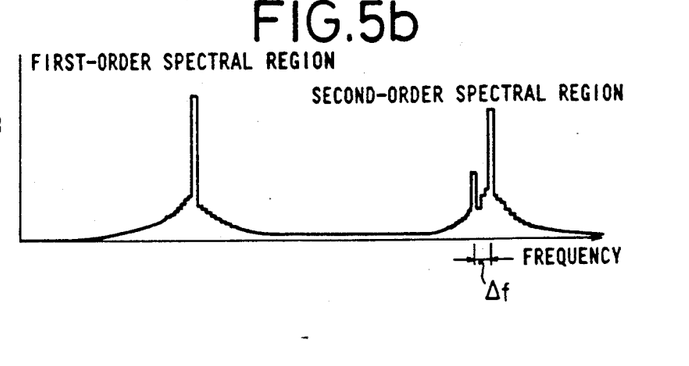

If a solid test object protrusion has a defect in either a thickness direction, a transverse direction, or a longitudinal direction, the defect having a length which is $\frac{1}{2}$ or more of the dimension of the test object in that direction, e.g., if the solid test object has a defect 13 having a length which is more than $\frac{1}{2}$ of the width H of the test object, as shown in FIG. 4A, there are observed two separate spectral energy peaks in a first-order spectral region corresponding to the protrusion with the defect 13, as shown in FIG. 5A. If the defect 13 has a length which is less than $\frac{1}{2}$ of the width H of the protrusion, as shown in FIG. 4B, there are observed two separate spectral energy peaks in a second-order spectral region corresponding to the protrusion, as shown in FIG. 5B.

If the test object has a trapped defect such as a blowhole or cavity rather than an exposed defect such as a crack, the trapped defect can also be similarly detected because there is observed a spectral energy peak induced by the trapped defect at a frequency lower than the frequency of the energy peak of a fundamental natural vibration in the second-order spectral region.

If a hollow cylindrical test object has a crack extending through its cylindrical wall, two separate spectral energy peaks are observed in the first-order spectral region because the crack, i.e., a through defect, is regarded as having a length which is more than $\frac{1}{2}$ of the width of the test object. If the hollow cylindrical test object has a trapped defect, two separate spectral energy peaks are observed in the second-order spectral region.

Figure 6:
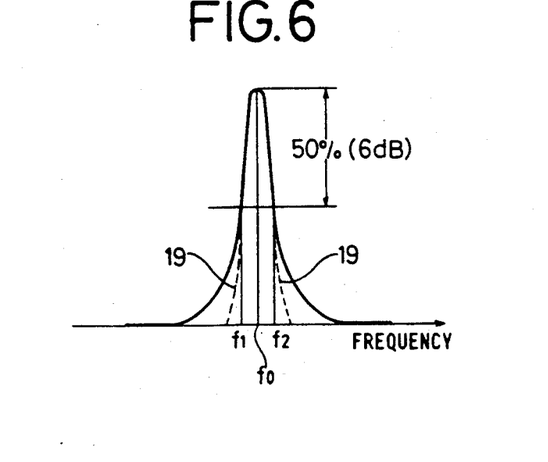
FIG. 6 is a diagram illustrative of Q or a value of sharpness of resonance or frequency selectivity with respect to frequencies at the time the test object is vibrated.

If a test object protrusion has a very small defect, the Q ($f1 - f2/f0$, see FIG. 6) of the spectral region corresponding to the protrusion is increased, resulting in a widened waveform. This appears to result from the fact that the spectral energy peak produced by the fundamental natural vibration and the spectral energy peak produced by the defect-induced vibration are observed as being coupled together, rather than separate from each other, because of the limited frequency resolution of a processing system.

Therefore, whether there is a defect or not in a test object protrusion can be determined by detecting the magnitude of the Q of the spectral region corresponding to the protrusion.

If a test object protrusion has a harder local region due to a spherical mass of graphite in a cast-iron structure, for example, there are observed two separate spectral energy peaks in the spectral region corresponding to the protrusion. The reason for this is given below.

In a substance, vibration is propagated at a velocity depending on the hardness of the substance. The higher the hardness, the faster the vibration is propagated in the substance. If a protrusion has a harder local portion therein, the harder portion increases the velocity of propagated vibration. Therefore, the vibratory energy is divided into the energy of a natural vibration and the energy of a vibration passing through the harder portion. Consequently, the spectral region corresponding to the protrusion has two separate energy peaks. Unlike the spectral energy peaks produced by the presence of a defect, the energy peak induced by the harder portion in the protrusion is located at a frequency higher than the frequency of a fundamental natural vibration.

If a test object protrusion has a softer local portion therein, the spectrum of the vibration of the protrusion contains a spectral energy peak of a fundamental natural vibration and a spectral energy peak of a vibration induced by the softer local portion, at a frequency lower than the frequency of fundamental natural vibration.

The sum of the energies of the energy peak of a fundamental natural vibration and the energy peak of the vibration induced by a defect or a different-hardness in a test object protrusion is equal to the energy of the spectral energy peak which would be produced if the protrusion had no defect or different-hardness portion, as shown in FIG. 3A.

The spectral energy peaks of the vibrations of the protrusions vary depending on the position in which the test object is vibrated. For example, when vibration is applied to the tip end of one protrusion, the spectral region corresponding to the protrusion has a large energy peak or peaks, but the spectral regions corresponding to the other protrusions have relatively small energy peaks. It may be difficult to determine whether there are two separate energy peaks in each of the spectral regions corresponding to those other protrusions. However, since an energy peak or peaks are large in the spectral region corresponding to a protrusion to which vibration is applied, it is easily to detect two separate energy peaks in that spectral region if the protrusion has a defect or different-hardness portion. Therefore, when each of the protrusions is positively vibrated, any defect or different-hardness portion in the protrusions can easily be detected by determining whether there are two separate energy peaks in each of the spectral regions corresponding to the protrusions. If vibration is applied to a protrusion exactly in a position where there is a defect or different-hardness portion then almost no energy peak induced by such a defect or different-hardness portion is produced. Therefore, vibration should be applied to each protrusion in at least two different positions in order to detect any defect or different-hardness portion reliably in the protrusions.

When the test object shown in FIG. 1 is inspected, vibration would have to be applied thereto twice at each of the six protrusions, and hence the test object would have to be vibrated twelve times. This procedure would be quite inefficient. According to the embodiment of the present invention, the test object is vibrated in at least two positions for the detection of a defect or different-hardness portion in each of the six protrusion.

More specifically, when a test object having a plurality of protrusions is vibrated in a certain position determined depending on the overall shape of the test object, all the protrusions can be vibrated uniformly. It is predicted that such uniform vibration of all the protrusions can be achieved when vibration is applied to the test object in the vicinity of the central cylindrical protrusion 1S. Such a position can be determined as follows:

The test object is vibrated in successive positions around the cylindrical protrusion 1S which are angularly spaced by a certain interval, e.g., 22°, and spectral energy peaks are observed in the spectral regions corresponding to the respective protrusions. Then, there is determined that one of the positions in which the test object is vibrated has energy peaks in the spectral regions with relatively uniform average magnitudes.

Figure 7:
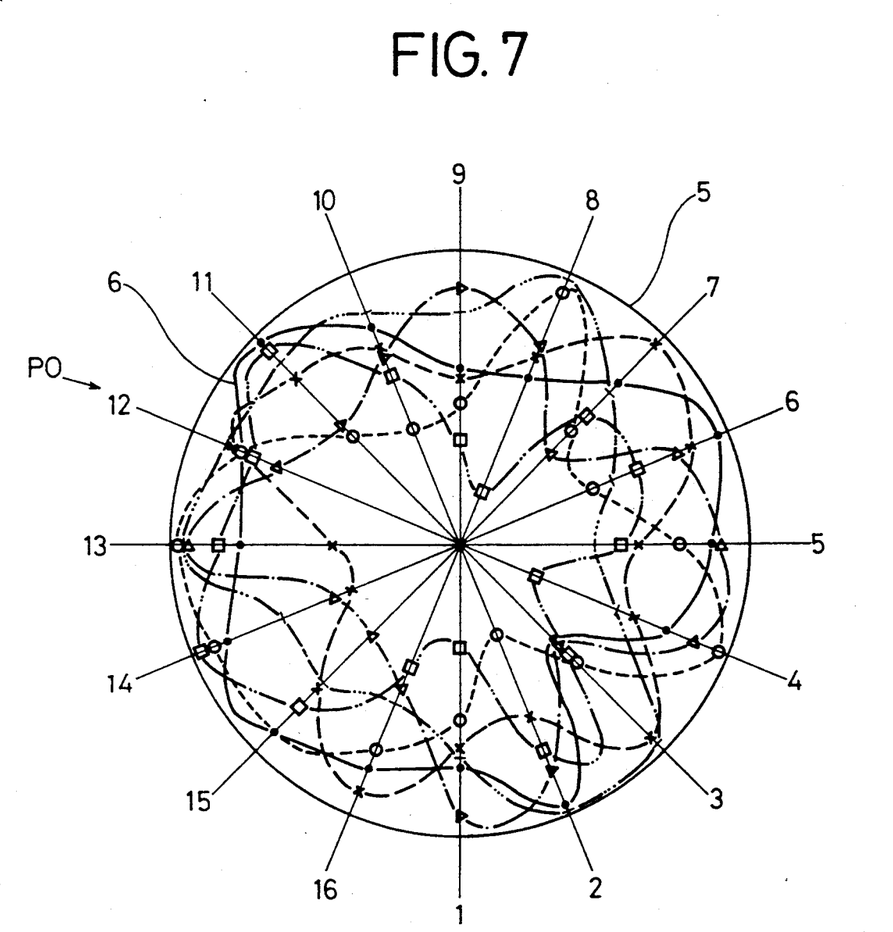
FIG. 7 is a diagram showing curves representing the loci of spectral energy peaks which are caused by the fundamental natural vibration of the protrusions of the test object.

For example, as shown in FIG. 7, a test object with six protrusions is vibrated in successive angular positions on and along an outer circumferential surface 5 of a cylindrical portion of the test object, and spectral energy peaks of a natural vibration of the six protrusions are plotted as distances from the center of the cylindrical portion when the test object is vibrated in those angular positions. Then, the loci 6 of those plotted energy peaks are drawn. From the loci 6, there is determined a position P0 where the energy peaks have relatively uniform magnitudes, and the position P0 is selected as a position in which vibration is to be applied to the test object for the detection of a defect or different-hardness portion.

When the test object is subsequently vibrated in the position P0, the energy spectral peaks in the spectral regions corresponding to all the protrusions have substantially equal values, making it possible to reliably detect any defect and/or a different-hardness portion in each of the protrusions.

Figure 8:
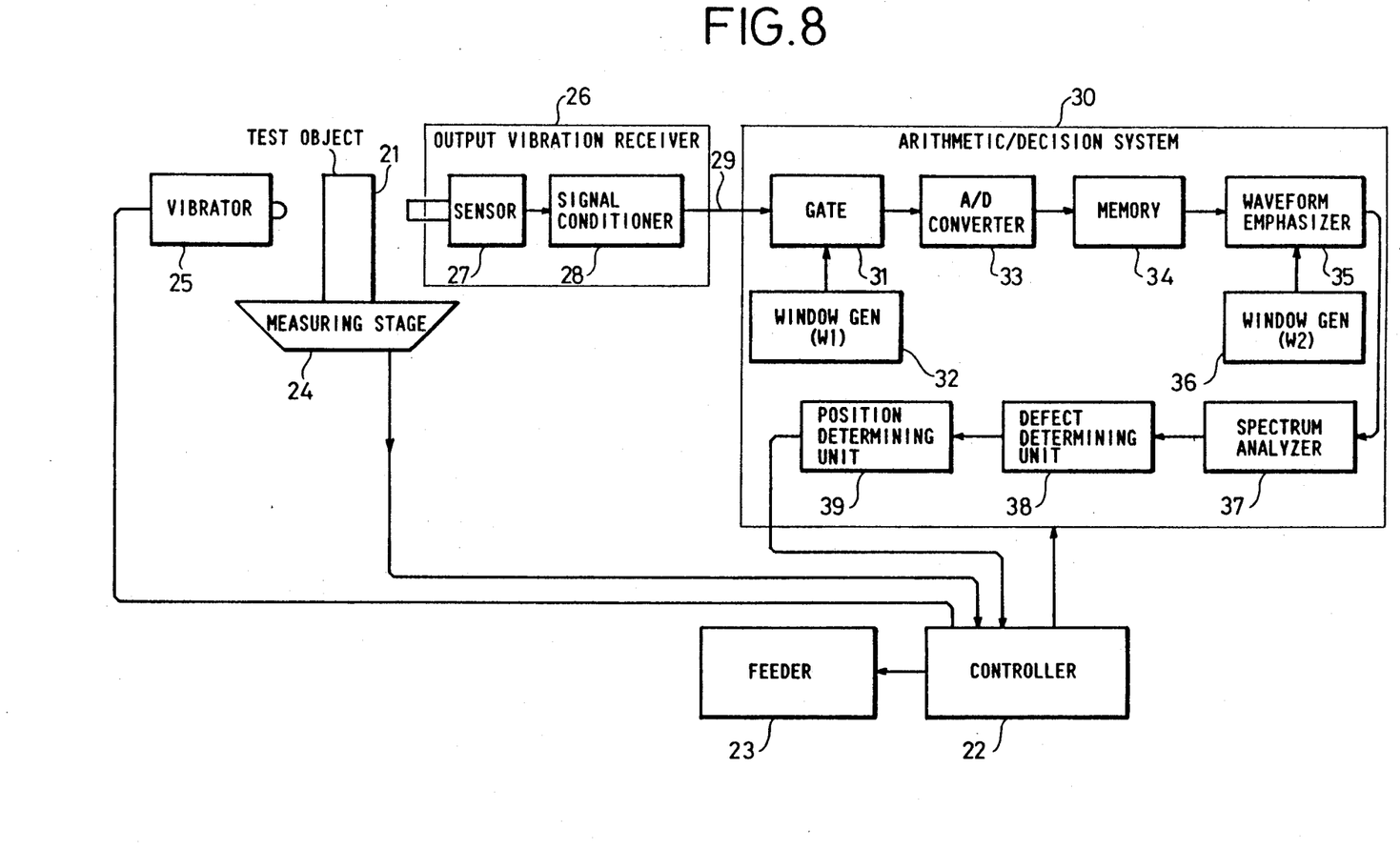
FIG. 8 is a block diagram of an apparatus for carrying out the method according to the present invention.

FIG. 8 shows an apparatus for carrying out the method according to the present invention to determine a defect and/or different-hardness portion and the position thereof.

A component, such as a test object 21, is fed along the production line by a feeder 23 which is controlled by a controller 23 which comprises a microcomputer, and placed on a measuring stage 24.

The measuring stage 24 is rotatable about its own axis and may be made of hard rubber, for example. When the test object 21 placed on the measuring stage 24 is detected by a detector (not shown) on the measuring stage 24, for example, the controller 22 actuates a vibrator 25 to vibrate the test object 21. For example, the vibrator 25 comprises a pendulum weight which is brought into hitting engagement with the test object 21 to exert an impulsive force or impact on the test object 21. The pendulum weight may be driven by a cam mechanism or the like, for example, which moves back the pendulum weight off the test object 21 immediately after the pendulum weight has hit the test object 21.

The vibrator 25 impacts the cylindrical test object 21 in two positions, i.e., the position P0 and a position which is angularly spaced by 22°, for example, from the position P0. The measuring stage 24 is rotatable in a horizontal plane, and the cylindrical test object 21 is placed thereon with its central axis aligned with the axis about which the measuring stage 24 is rotatable.

First, the test object 21 is vibrated in the position P0 on its outer circumference by the vibrator 25. Thereafter, the measuring stage 24 is turned through 22°, and the test object 21 is vibrated in the second position.

The vibration of the vibrated test object 21 is detected by a sensor 27 of an output vibration receiver 26 in a noncontact manner, and converted thereby into an electric signal, which is then processed by a signal conditioner 28. The sensor 27 may be any known type which detects vibrations, e.g., a displacement meter or the like. However, the sensor 27 should preferably have sharp directivity toward the test object 21 so to pick up ambient noise vibrations.

The signal conditioner 28 amplifies the electric signal from the sensor 27, and remove unnecessary high-frequency and low-frequency components from the signal.

The electric signal from the output vibration receiver 26 is supplied through a transmission cable 29 to an arithmetic/decision system 30. The arithmetic/decision system 30 comprises a microcomputer, for example, that is programmed to effect various arithmetic and decision operations (described later). The software-implemented functions of the arithmetic/decision system 30 are shown in FIG. 8.

When the test object is subjected to forced vibration, the forced vibration produces an initial longitudinal wave which is mixed with the natural vibration. If a defect in the test object is a considerably large crack or cavity, then such a defect can be detected without being adversely affected by the mixed longitudinal wave. Usually, however, defects cannot be detected unless vibrations other than the natural vibration are removed as much as possible.

Removal of such other vibrations is effected in the apparatus shown in FIG. 7 as follows:

Two processes, i.e., the sine-wave process and the impulse process, are available for applying vibration to the test object 21. In the sine-wave process, vibration is applied to the test object 21 under certain conditions, and then the application of vibration is stopped at a certain instant. Upon elapse of a certain time after the stoppage of the application of vibration, the vibration of the test object 21 starts being measured. In the impulse process, the vibration of the test object 21 starts being measured upon elapse of a certain time after the test object 21 is vibrated by an impulsive impact.

The time which elapses before the vibration measurement after the application of vibration is stopped o the impact is applied, is determined as follows: The velocity c of a sound wave propagated in the test object 21 varies depending on the Young's modulus E (modulus of elasticity) and the density $\rho$ of the material of the test object 21, and is expressed by the following equation:

$$c = \sqrt{\frac{E}{\rho}}.$$

Figure 9A:
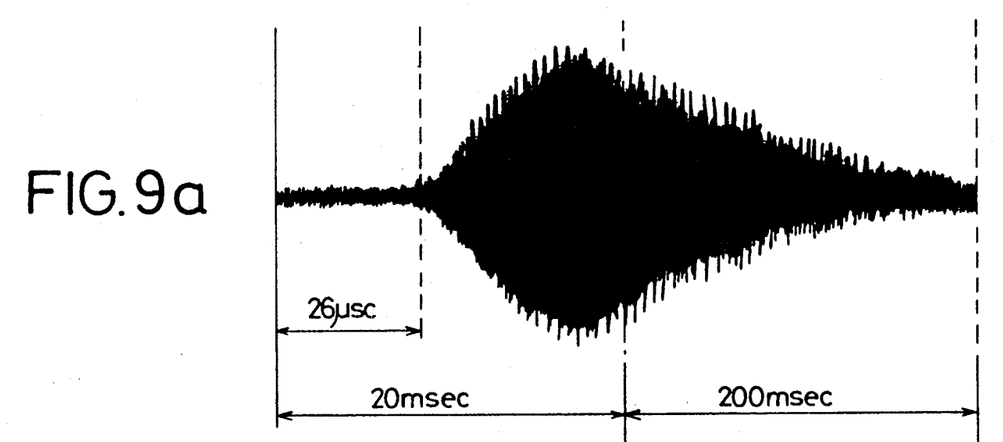
FIGS. 9A, 9B, and 9C are diagrams showing the waveforms of natural vibrations of the test object, an extracting window, and an emphasizing window.

For example, if the test object 21 is in the form of a cast-iron cylinder and vibrated by the impulse process, the velocity of the longitudinal wave in the test object 21 is 4560 m/s, and the velocity of the transverse wave in the test object 21 is 1/1.8 times the velocity of the longitudinal wave, i.e., about 2780 m/s. FIG. 9A shows a waveform in the time domain of the vibration of the test object 21 which is picked up immediately after the application of the impact. As shown in FIG. 9A, only the faster longitudinal wave continues for about 26 μsec., and thereafter the transverse wave is detected. After the peak of the transverse wave, the vibration is exponentially attenuated until it stops.

Since the vibration of the test object 21 is identical to the vibration caused by an earthquake, the vibration is composed of a mixture of faster and slower waves. Moreover, the forced vibration remains in the vibration of the test object 21. As a result, the waveform shown in FIG. 9A is not representative of the natural vibration inherent in the configuration of the test object 21. The waveform of the inherent natural vibration is considered to be observed slightly before the vibration stops, just like the "precession" of a spinning top. Therefore, the vibration of the test object 21 is extracted after it has started being attenuated past the peak of the transverse wave. The vibration of the test object 21 after the peak of the transverse wave is extracted using a rectangular extracting window W1 as shown in FIG. 9B.

The window W1 generated by a window generator 32 extracts the natural vibration inherent in the test object 21 from the vibration of the test object 21 in a gate 31 to which the electric signal is supplied from the output vibration receiver 26.

Figures 9B, 9C:
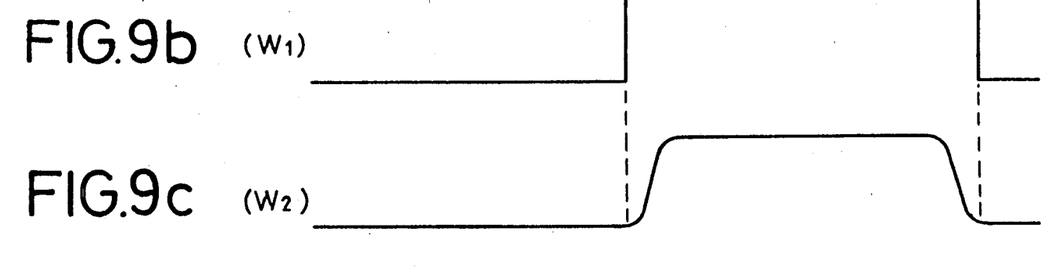

In FIG. 9B, the window W1 has a leading edge which rises 20 msec. after the impact is applied to the test object 21. The window W1 has a duration of 200 msec. The window generator 32 generates the window W1 based on a control signal from the controller 22 which indicates the start of the vibration of the test object 21.

The natural-vibration component thus extracted with the window W1 is then converted by an A/D converter 33 into digital data which is thereafter stored in a memory 34. The stored digital data is then read from the memory 34, and processed by a waveform emphasizer 35 with a waveform-emphasizing window W2 generated by another window generator 36. The window W2 is generated based on the control signal from the controller 22 which indicates the start of the vibration of the test object 21.

The window W2 will be described below. A vibration waveform produced by a small crack, cavity, blowhole, or other defect is apt to be included in the extracted natural-vibration waveform inherent with the test object 21, and can be detected relying upon the Q or sharpness of frequency selectivity. It may also be possible to reduce the width of the spreading portion of the spectral peak waveform of fundamental natural vibration for easier determination of a crack, blowhole, or the like. One approach is to correct the signal to sharply attenuate the signal amplitude below 50% of the peak (without varying the Q) as indicated by the broken lines 19 in FIG. 6. With the signal thus emphasized, the spreading portion of the spectral peak waveform is reduced in width, so that a spectral energy peak induced by a small defect in the test object 21 can be detected as being distinguished from the spectral energy peak of fundamental natural vibration, without relying on the Q.

To emphasize the spectral peak waveform, the signal from the memory 34 which is indicative of the extracted natural-vibration component is processed by the window W2 that is expressed by the following equation:

$$y = a\cos^2(x\omega t) + b\cos^2(x\omega t + \tau) + \ldots + k\cos^2(x\omega t + n\tau) + C$$

where $\tau$ is a time lag which may be $\lambda/4$ ($\lambda$ is the wavelength) and $a = b = \ldots = k$. The window W2 has a waveform as shown in FIG. 9C.

Figure 10A:
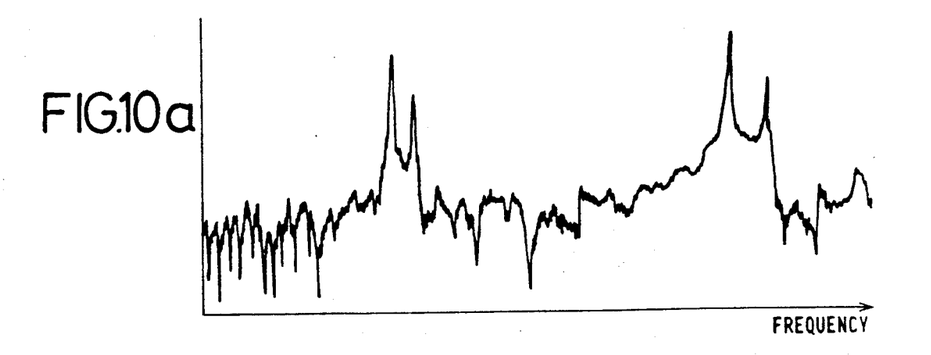
FIGS. 10A, 10B, and 10C are diagrams showing the waveforms of natural vibrations of the test object, after they are produced, after they are processed with the extracting window, and after they are processed with the emphasizing window.
Figure 10B:
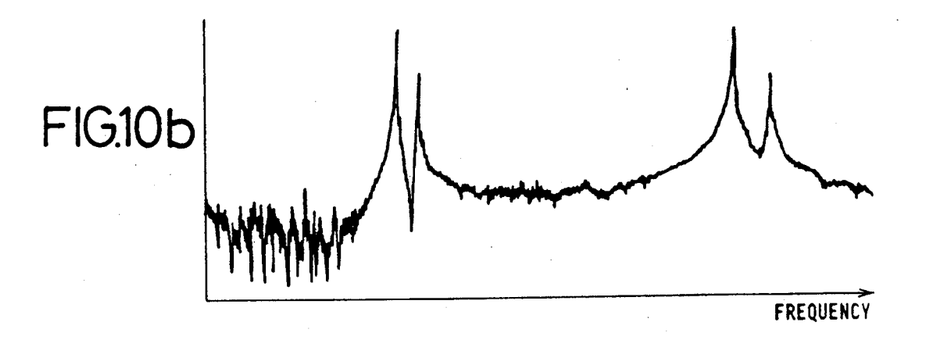
Figure 10C:
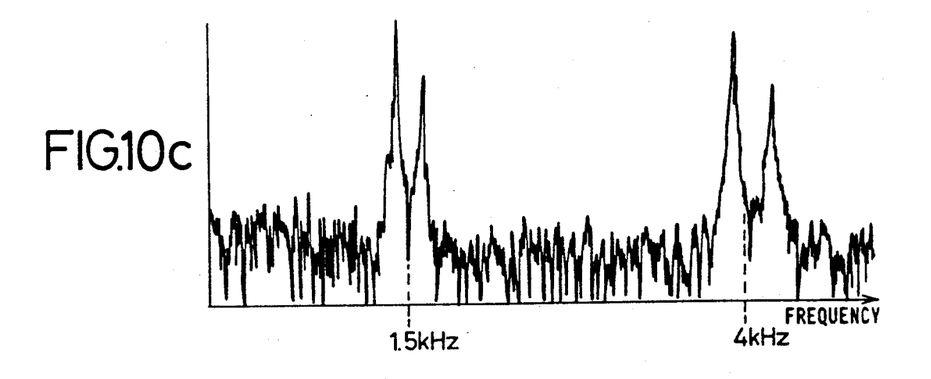

FIG. 10A shows a spectrum of the picked-up vibration of the test object 21 before being processed with the windows W1, W2. FIG. 10B shows a spectrum of the vibration which is extracted with the window W1 upon elapse of 20 msec. immediately after the test object 21 has started being vibrated. It can be seen from FIG. 10B that an energy peak of fundamental natural vibration and a defect-induced energy peak are observed as being separated from each other. FIG. 10C shows a spectrum of the vibration which is emphasized with the window W2, indicating that the energy peak of a fundamental natural vibration and the defect-induced energy peak are more clearly separated from each other.

The waveform-emphasized data is thereafter supplied to a spectrum analyzer 37 for spectral analysis.

Spectral data from the spectrum analyzer 37, as shown in FIGS. 3A and 3B, are then sent to a defect determining unit 38. The defect determining unit 38 determines whether there is a defect-induced energy peak in each of the spectral regions corresponding to the protrusions to detect whether there is a defect in each of the protrusions.

Figure 11:
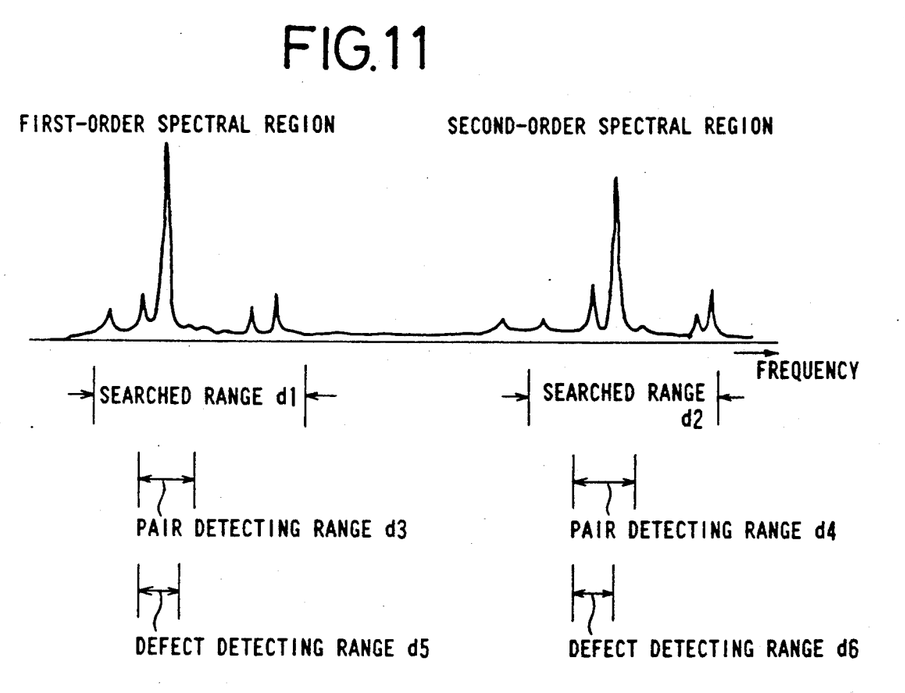
FIG. 11 is a diagram illustrative of the manner in which a defect is determined by a defect determining unit in the apparatus shown in FIG. 8.

The defect determining unit 38 searches each of the spectral regions in the vicinity of the frequencies of energy peaks therein, and determine whether there are two separate energy peaks in each of the spectral regions. More specifically, as shown in FIG. 11, the defect determining unit 38 determines, from the spectrum analyzer 37, five energy peaks successively in order from the greatest amplitude in each of a first-order spectral frequency range d1 and a second-order spectral frequency range d2 for the spectral region corresponding to each of the protrusions, and stores the values of the energy peaks and the frequencies thereof. Then, the defect determining unit 38 searches the stored frequencies for any pair of energy peaks whose frequencies fall within preset frequency ranges d3, d4 (d3, d4 < d1, d2) with respect to both the first-order and second-order spectral regions. These frequency ranges d3, d4 are determined in advance such that the ranges will contain a pair of an energy peak of a fundamental natural vibration and an energy peak of a vibration induced by a defect. If such a pair is detected within the frequency range d3 in the first-order spectra region, then the defect determining unit 38 determines the higher frequency of a lower-frequency pair as the position of a first-order energy peak of a fundamental natural vibration. The defect determining unit 38 then determines whether there is an energy peak (which may be a pair of energy peaks) other than the determined energy peak of a fundamental natural vibration, within a preset frequency range d5 that is narrower than the frequency range d3. If there is an energy peak within the frequency range d5, the defect determining unit 38 determines that there is a defect, larger than ½ of the width, in the protrusion.

If a pair of energy peaks is detected within the frequency range d4 in the second-order spectral region, the defect determining unit 38 determines the higher frequency of a lower-frequency pair as the position of a second-order energy peak of a fundamental natural vibration. The defect determining unit 38 then determines whether there is an energy peak other than the determined energy peak of fundamental natural vibration, within a preset frequency range d6 that is narrower than the frequency range d4. If there is an energy peak within the frequency range d6, the defect determining unit 38 determines that there is a defect, smaller than ½ the width, in the protrusion.

Figure 12:
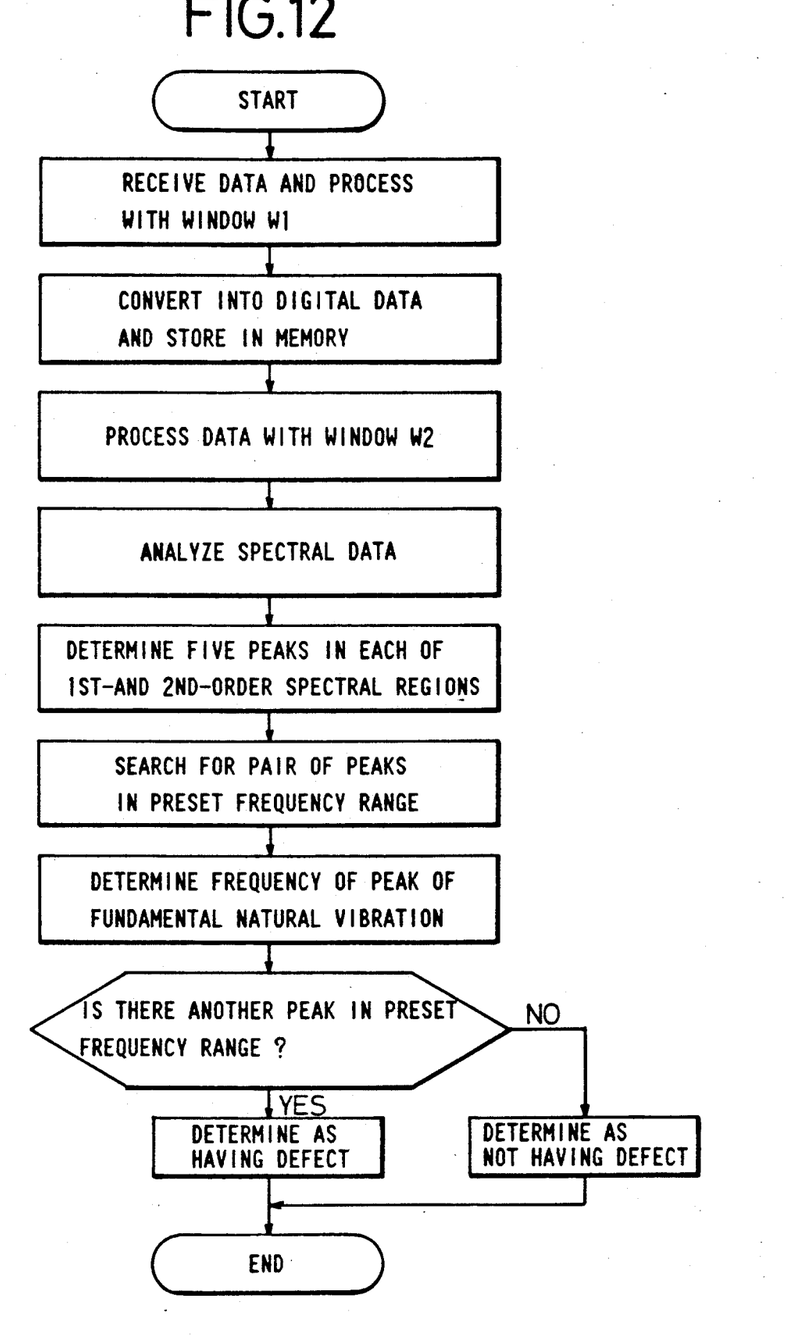
FIG. 12 is a flowchart of an operation sequence of the apparatus shown in FIG. 8.

The above operation sequence of the arithmetic/decision system 30 is shown in the flowchart of FIG. 12.

The above operation sequence is carried out with respect to the spectral regions corresponding to all the protrusions to determine whether there is a defect in each of the protrusions.

If it is determined by the defect determining unit 38 that the test object 21 has a defect in one or more protrusions, a position determining unit 39 determines which of the protrusions contains the defect.

The protrusion of the test object 21 where a defect may possibly be present is marked with a paint by a marker applicator (not shown). The positions where a defect larger than ½ of the width may possibly exist and the positions where a defect smaller than ½ of the width may possibly exist may be marked in different marker colors so that the defects can be distinguished from each other.

In the above embodiment, the test object 21 is vibrated in a minimum number of positions for determining positions where a defect may possibly be present. However, it is also possible to apply vibration successively to all the protrusions of the test object 21 for the determination of a defect.

Whether there is a different-hardness portion in protrusions can also be determined in the same manner as described above. However, if a harder local portion is to be detected, it is determined whether a spectral energy peak of vibration induced by such a harder local portion is present as one of a peak pair at a frequency higher than the frequency of the energy peak of a fundamental natural vibration.

In the above embodiment, the test object has six protrusions. However, the principles of the present invention are applicable to test objects having more or less protrusions.

The test object may be vibrated according to any of various processes other than the impulse process. For example, one end of the test object may be fixed and the other end may be deflected for vibration.

With the present invention, as described above, a test object having a plurality of protrusions is vibrated, and the natural vibrations of the protrusions are detected by a sensor not in contact therewith. The spectral data of the vibrations is analyzed to detect whether each of the protrusions contains a defect and/or a different-hardness portion. Stated otherwise, it is easily determined which of the protrusions contains a defect and/or a different-hardness portion.

Because defects and/or different-hardness portions and their positions are determined by detecting the natural vibration of the test object in a noncontact fashion, the waveform of the vibration is simple and easy to determine as it is not adversely affected by irregular reflections which would otherwise be caused if the sensor were held in contact with the test object through inadequate coupling. Therefore, it can be determined whether the protrusions of the test object have a defect and/or a different-hardness portion therein or not, through stable measurements without disturbance.

Even if the test object has wrinkles or surface irregularities, a defect and/or a different-hardness portion can reliably be detected provided defect-induced vibrations can be distinguished from the natural vibration.

All the protrusions can be inspected for defects and/or different-hardness portions simply by applying vibration of the test object in at least one position determined by the configuration of the test object.

Although certain preferred embodiments have been shown and described, it should be understood that many changes and modifications may be made therein without departing from the scope of the appended claims.

What is claimed is:

1. A method of detecting a defect and/or a different-hardness portion in a test object having a plurality of protrusions, comprising the steps of:
    (a) applying a mechanical vibration to a test object having a plurality of protrusions;
    (b) analyzing spectral data of the vibration of the test object based on signals indicative of the vibration of the protrusions;
    (c) detecting spectral energy peaks in different spectral frequency regions corresponding respectively to the protrusions based on the signals; and
    (d) determining whether two separate spectral energy peaks are in the spectral frequency region corresponding to each protrusion, thereby determining whether a defect or a different-hardness portion is in each of the protrusions.

2. The method according to claim 1, wherein the signals indicative of the vibration of the test object represent at least first-order and second-order spectral data of the vibration and further comprising the steps of:
    (e) detecting, from the first-order and second-order spectral data, a spectral energy peak of a natural vibration of the test object and a spectral energy peak of a defect-induced vibration of the test object; and
    (f) determining that a defect is in the test object when the spectral energy peak of the defect-induced vibration is detected.

3. The method according to claim 2, further comprising the steps of:
    (g) establishing a frequency range with respect to the first-order or second-order spectral data;
    (h) detecting a plurality of spectral energy peaks in order from a greater amplitude within the frequency range;
    (i) determining whether the frequencies of the detected spectral energy peaks fall in a detection range defined by the natural frequency of the test object and a defect-induced frequency;
    (j) determining, when at least two spectral energy peaks are in the detection range, that one of the spectral energy peaks is caused by the natural vibration of the test object and the other spectral energy peak is caused by the vibration induced by a defect in the test object; and
    (k) determining that there is a defect in the test object based on the other spectral energy peak.

4. The method according to claim 3, further comprising the steps of:
    (l) setting a frequency range with one of the spectral energy peaks at its center after the one of the spectral energy peaks is determined as being caused by the natural vibration of the test object; and (m) determining that any spectral energy peak in the frequency range established in said step (l) as being caused by a defect in the test object.

5. A method according to claim 1, further comprising the steps of:
   (e) detecting a position where the spectral energy peaks in the spectral regions corresponding respectively to the protrusions have substantially a same amplitude; and
   (f) determining the position as a position where vibration is applied to the test object.

6. An apparatus for detecting a defect and/or a different-hardness portion in a test object having a plurality of protrusions, comprising:
   vibrating means for mechanically vibrating a test object having a plurality of protrusions;
   detecting means for detecting vibration of the test object and for converting the detected vibration into data representing frequencies of the detected vibration;
   means, responsive to said data from said detecting means, for analyzing a spectrum of said data representing the vibration of the test object to detect spectral energy peaks in respective spectral frequency regions corresponding respectively to the protrusions; and
   determining means for determining, when two separate spectral energy peaks are in each of the spectral frequency regions, that a defect or a different-hardness portion is present in the protrusion.

7. The apparatus according to claim 6, further comprising:
   a rotatable measuring stage for supporting the test object thereon;
   said rotatable measuring stage including an elastic member.

8. The apparatus according to claim 6, wherein said determining means comprises:
   gate means for introducing, at a predetermined time interval, a signal indicative of a natural vibration and a defect-induced vibration of the test object;
   memory means, connected to an output terminal of said gate means, for storing the signal from said gate means;
   spectrum analyzing means, connected to an output terminal of said memory means, for processing spectral data corresponding to said signal indicative of a natural vibration of the test object and a defect-induced vibration of the test object; and
   defect determining means, connected to an output terminal of said spectrum analyzing means, for determining whether a defect is in each protrusion based on the processed spectral data.

9. The apparatus according to claim 6, further comprising:
   position detection means for detecting a position where the spectral energy peaks in the spectral regions corresponding respectively to the protrusions have substantially a same amplitude.

10. The apparatus according to claim 7, further comprising;
   detecting means for detecting a position where the spectral energy peaks in the spectral regions corresponding respectively to the protrusions have substantially a same amplitude.

11. The apparatus according to claim 8, further comprising:
   detecting means for detecting a position where the spectral energy peaks in the spectral regions corresponding respectively to the protrusions have substantially a same amplitude.

12. The method according to claim 2, further comprising the steps of:
   (g) detecting a position where the spectral energy peaks in the spectral regions corresponding respectively to the protrusions have substantially a same amplitude; and
   (h) determining the position as a position where vibration is applied to the test object.

13. The method according to claim 3, further comprising the steps of:
   (l) detecting a position where the spectral energy peaks in the spectral regions corresponding respectively to the protrusions have substantially a same amplitude; and
   (m) determining the position as a position where vibration is applied to the test object.

14. The method according to claim 4, further comprising the steps of:
   (n) detecting a position where the spectral energy peaks in the spectral regions corresponding respectively to the protrusions have substantially a same amplitude; and
   (o) determining the position as a position where vibration is applied to the test object.

* * * * *